Figure 1:
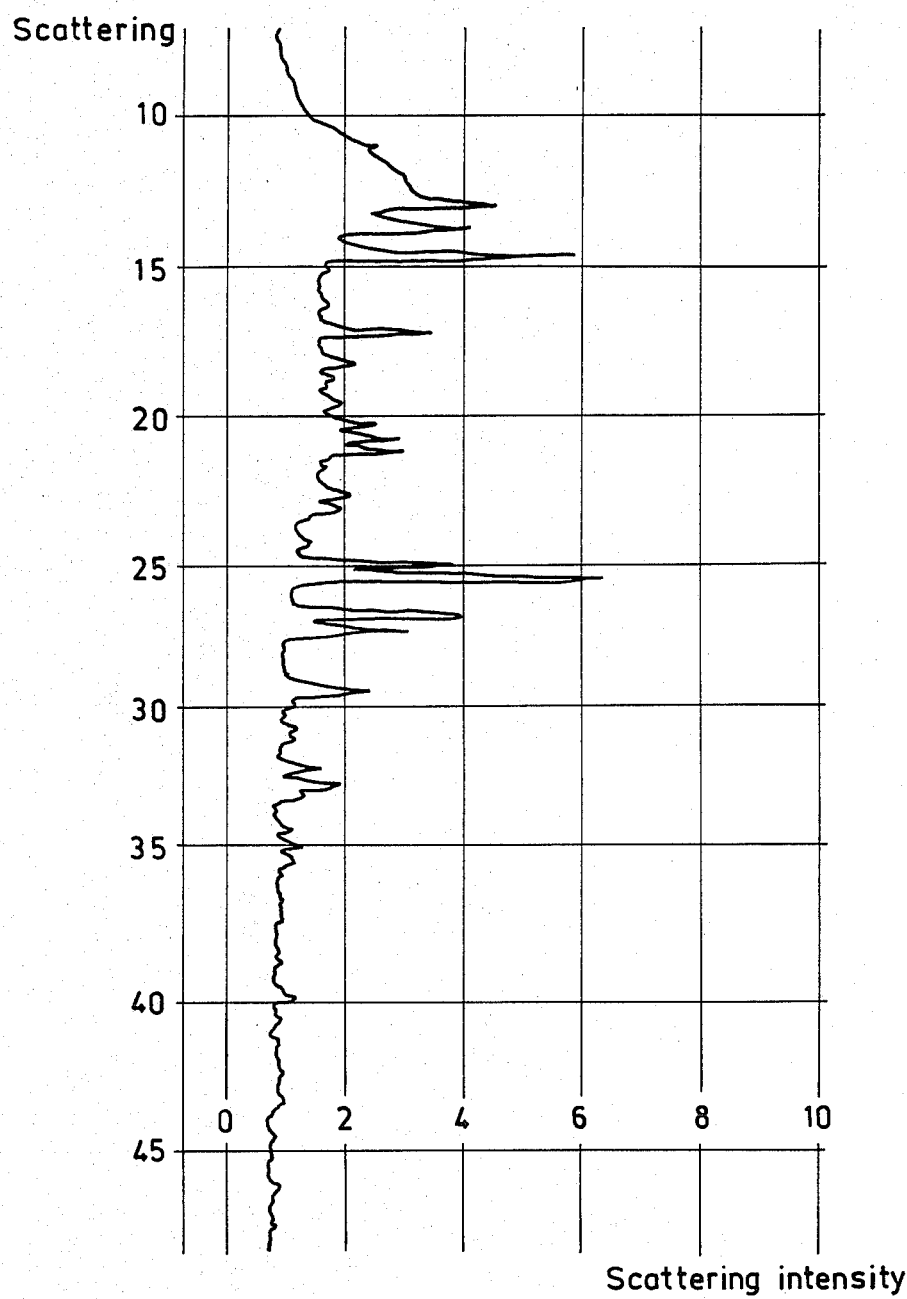

United States Patent [19]

Kreidl et al.

[11] Patent Number: 4,537,900

[45] Date of Patent: Aug. 27, 1985

[54] CIMETIDINE Z, A NEW CRYSTAL MODIFICATION OF CIMETIDINE

[75] Inventors: János Kreidl; Maria Farkas née Kirják; Kalmán Harsányi; Belá Benke; András Radó; György Domany; Béla Hegedüs; Éva Csongor; Ida Deutsch née Juhász; Hajnalka Pethö, all of Budapest, Hungary

[73] Assignee: Richter Gedeon Vegyészeti Gyar R.T., Budapest, Hungary

[21] Appl. No.: 632,311

[22] Filed: Jul. 20, 1984

Related U.S. Application Data

[63] Continuation of Ser. No. 423,074, Sep. 24, 1982, abandoned.

[30] Foreign Application Priority Data

Sep. 25, 1981 [HU] Hungary ............................. 2767/81

[51] Int. Cl.³ .................. A61K 31/415; C07D 233/64
[52] U.S. Cl. ..................................... 514/400; 548/342
[58] Field of Search ..................... 548/342; 424/273 R

[56] References Cited

FOREIGN PATENT DOCUMENTS 2742531 3/1978 Fed. Rep. of Germany ...... 548/342

OTHER PUBLICATIONS

Prodic-Kojic, B., et al., *Gazz. Chim. Ital.*, 109, 535 (1979).

*Primary Examiner*—Richard A. Schwartz
*Attorney, Agent, or Firm*—Keil & Weinkauf

[57] ABSTRACT

The invention relates to a new crystal modification of N-methyl-N'-{2-[(5-methylimidazol-4-yl)-methylthio]-ethyl}-N"-cyanoguanidine (cimetidine), a histamine H-2 receptor antagonist having the Formula (I)

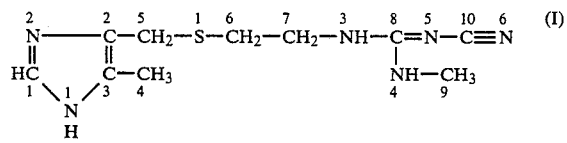

as well as to a process for preparing same. In the description, this new modification is named N-methyl-N'-{2-[(5-methylimidazol-4-yl)-methylthio]-ethyl}-N"-cyanoguanidine Z (cimetidine Z).

3 Claims, 2 Drawing Figures

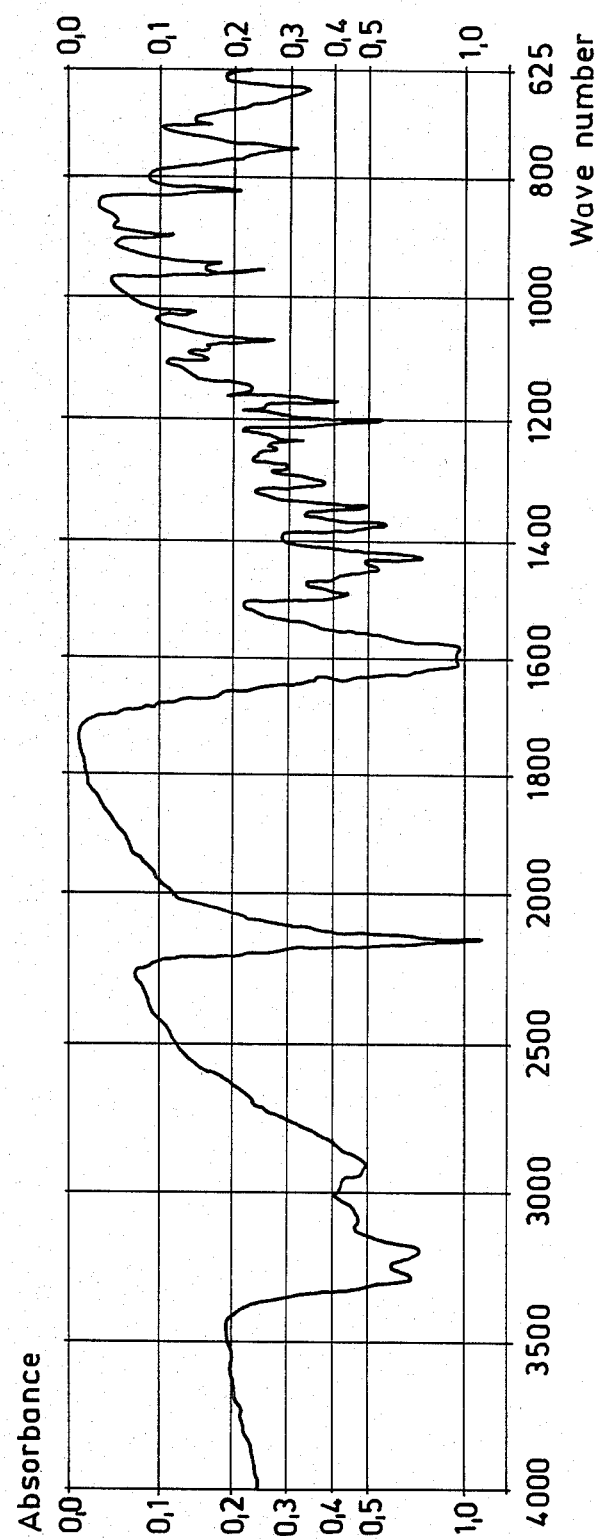
Fig. II

CIMETIDINE Z, A NEW CRYSTAL MODIFICATION OF CIMETIDINE

This application is a continuation of application Ser. No. 423,074, filed Sept, 24, 1982, now abandoned.

This invention relates to a new crystal modification of N-methyl-N'-{2-[(5-methylimidazol-4-yl)-methylthio]-ethyl}-N''-cyanoguanidine (cimetidine), a histamine H-2 receptor antagonist having the Formula (I)

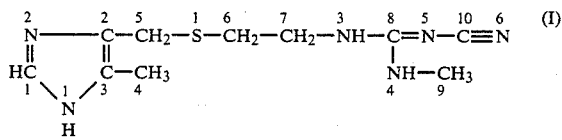

as well as to a process for preparing same. In this description, this new modification is named N-methyl-N'-{2-[(5-methylimidazol-4-yl)-methylthio]-ethyl}-N''-cyanoguanidine Z (cimetidine Z).

Several modifications of N-methyl-N'-{2-[(5-methylimidazol-4-yl)-methylthio]-ethyl}-N''-cyanoguanidine have been described in the literature. According to the published German patent application No. 2,742,531 the modification A, which is most useful for pharmaceutical purposes, is formed by crystallization from anhydrous media, while modification B or C, respectively, separates from a solvent containing water.

Similar statements are contained in an other publication [Gazz. Chim. Ital. 109, 535 (1979)]. The main conclusion of the latter is that the separation of the individual modifications from an aqueous medium is accidental and cannot be controlled.

From the processes known for the preparation of N-methyl-N'-{2-[(5-methylimidazol-4-yl)-methylthio]-ethyl}-N''-cyanoguanidine those described in the Belgian patent No. 804,144 have practical importance. These are as follows:

(a) the reaction with ethanolic methylamine of N-cyano-N'-{2-[(5-methylimidazol-4-yl)-methylthio]-ethyl}-S-methylisothiourea;

(b) the reaction of 4-[2-(aminoethyl)-thiomethyl]-5-methylimidazole with N-cyano-N',S-dimethylisothiourea in acetonitrile by boiling for a long time;

(c) the reaction of N-methyl-N'-{2-[(5-methylimidazol-4-yl)-methylthio]-ethyl}-thiourea with lead cyanimide in a mixture of dimethylformamide and acetonitrile.

All these processes are carried out in anhydrous media. According to the process (b), the product is obtained with a yield of only 20% after purifying with column chromatography [J. Med. Chem. 20, 901 (1977)]. The yield of the process (c) (i.e. 40%) also falls below the effectivity required in the last step of a reaction sequence. Another disadvantage of process (c) is the use of a lead reagent.

Although process (a) seems to be problem-free concerning the yield, the carrying out of the reaction and working up of the reaction mixture is rather problematic. According to the Belgian patent No. 804,144 (Example 1 (c) /ii/), the reaction takes place at room temperature with a large excess of methylamine in ethanol, the mixture is then evaporated and the residue recrystallized from a mixture of isopropanol and petroleum ether. The inconveniences of this method can be summarized as follows. Methyl mercaptan, arising from the condensation reaction, does not leave the system in the course of the reaction carried out at room temperature and as a consequence, the simultaneous leaving of both gases proceeds during evaporation so violently that the binding of these gases cannot be solved. N-methyl-N'-{2-[(5-methylimidazol-4-yl)-methylthio]-ethyl}-N''-cyanoguanidine as the reaction product appears as an evaporation residue containing all contaminations and side products. These cannot be removed in the way described in the Example cited from the Belgian patent No. 804,144; thus, the recrystallization does not result in a product of the required quality.

When preparing N-methyl-N'-{2-[(5-methylimidazol-4-yl)-methylthio]-ethyl}-N''-cyanoguanidine in anhydrous media, the recrystallization and purification to a certain but not satisfying degree of the compound can be solved by the recrystallization from an anhydrous organic solvent. This leads to N-methyl-N'-{2-[(5-methylimidazol-4-yl)-methylthio]-ethyl}-N''-cyanoguanidine A which is the most useful modification for pharmaceutical purposes.

During our experiments aimed at improving the chemical preparation of N-methyl-N'{2-[(5-methylimidazol-4-yl)-methylthio]-ethyl}-N-''-cyanoguanidine, it was found that in case of the reaction of N-cyano-N'{2-[(5-methylimidazol-4-yl)-methylthio]-ethyl}-S-methylisothiourea with methylamine in aqueous media, temperature conditions could be found under which the evolution of methyl mercaptan became smooth; thus, the destruction (annihilation) of same by chemical transformation (burning, oxidation with hypochlorite) could be accomplished more favourably in comparison to the abrupt gas evolution. Namely, the leaving of methyl mercaptan is retarded by methylamine (because of a loose salt formation) at or even above room temperature, while on heating in ethanolic media, the methylamine reactant also steps out to a significant extent. On the contrary, when an aqueous medium is used, methyl mercaptan can be eliminated at temperatures far below the boiling point (at about 50°-60° C.). Thus, methylamine can be used in a lower excess, i.e. more economically: 2 to 5 moles of it are satisfying for the rapid and complete transformation, as opposed to the 10 moles required according to the literature.

The advantages of the process carried out in an aqueous medium concern not only the safety and protection of the environment. Additional advantages are the decrease in the amount of methylamine used and the fact that the N-methyl-N'-{2-[(5-methylimidazol-4-yl)-methylthio]-ethyl}-N''-cyanoguanidine obtained is purer.

Namely, S,S'-bis-[2-(N-cyano-N-'-methyl)-guanidino-ethyl]-disulphide appears as a side product in the reaction. The preparation of this compound is described in the published German patent application No. 2,944,257 (though with a not satisfying purity). The contamination with disulphide of cysteamine hydrochloride, used for the precursor of the synthesis, is not necessary for the appearance of this compound as impurity. The formation of this substance can be formulated from bis-(2-aminoethyl)-disulphide (contaiminating the cysteamine), methyl N-cyanoimidodithiocarbonate and methylamine but, according to our discovery, it can also arise from splitting of the C-S bond in the side chain of N-methyl-N'-{2-[(5-methylimidazol-4-yl)-methylthio]-ethyl}-N''-cyanoguanidine. The interchange of various nucleophills in Mannich type compounds is well known. It was found that the above contamination, crystallizing together with the desired product from organic solvents, can be removed even by crystallization from water, or by a reaction carried out in water and by washing thoroughly out the methylamine with water before drying. On the basis of our experiments, the amount of the contaminating side product considerably increases when the reaction is realized by boiling with the methylamine solution or when the drying is performed in the presence of methylamine. This can be proved by thin layer chromatography on Kieselgel 60F 254 adsorbent, by development with a 5:4:1 ethyl acetate-acetone-water system and by evaluation with UV densitometry of the spot appearing with 0.45 $R_f$ value.

The preparation with aqueous methylamine of N-methyl-N'-{2-[(5-methylimidazol-4-yl)-methylthio]-ethyl}-N''-cyanoguanidine is favourable both for carrying out the reaction as well as for obtaining a substance with higher purity. During the practical verification of these advantages, it was aimed to develop a simple process for obtaining N-methyl-N'{2-[(5-methylimidazol-4-yl)-methylthio]-ethyl}-N''-cyanoguanidine from the aqueous reaction mixture as well as for the preparation of modification A.

When investigating the conditions for the precipitation from media containing water or water together with an organic solvent, it was surprisingly found that when the precipitation takes place at 10° to 50° C., preferably at 20° to 40° C., N-methyl-N'-{2-[(5-methylimidazol-4-yl)-methylthio]-ethyl}-N''-cyanoguanidine appears with a new crystal form which can well be handled, easily filtered and washed. This new crystal modification can be verified by spectroscopy and X-ray diffraction and is named N-methyl-N'-{2-[(5-methylimidazol-4-yl)-methylthio]-ethyl}-N''-cyanoguanidine Z (cimetidine Z). When filtering out this form from an aqueous medium, it retains approximately 3 to 15% of mother liquor and can be purified from the contaminations being present in the mother liquor by a single washing-out. N-methyl-N'-{2-[(5-methylimidazol-4-yl)-methylthio]-ethyl}-N''-cyanoguanidine Z can also be prepared by seeding a supersaturated aqueous or organic solution (e.g. in methanol) with a crystal of the N-methyl-N'-{2-[(5-methylimidazol-4-yl)-methylthio]-ethyl}-N''-cyanoguanidine Z form.

From N-methyl-N'-{2-[(5-methylimidazol-4-yl)-methylthio]-ethyl}-N''-cyanoguanidine Z the therapeutically more significant modification A can be prepared in a manner known in the art, i.e. by recrystallization from an organic solvent, preferably from isopropanol. This recrystallization can also be directly carried out with the crude product containing water.

Thus, this invention relates to the new crystal modification Z of N-methyl-N'-{2-[(5-methylimidazol-4-yl)-methylthio]-ethyl}-N''-cyanoguanidine as well as to a process for preparing same, which comprises (a) precipitating N-methyl-N'-{2-[(5-methylimidazol-4-yl)-methylthio]-ethyl}-N''-cyanoguanidine at 10° to 50° C., preferably at 20° to 40° C., from a supersaturated solution formed with water or with water and a water-miscible organic solvent, or, (b) crystallizing out N-methyl-N'-{2-[(5-methylimidazol-4-yl)-methylthio]-ethyl}-N''-cyanoguanidine from a supersaturated solution by seeding with a crystal of the N-methyl-N'-{2-[(5-methylimidazol-4-yl)-methylthio]-ethyl}-N''-cyanoguanidine Z form.

The infrared examinations of the new crystal modification were accomplished in such a way that a sample weighing 1.5 mg was homogenized with 300 mg of KBr and pellets were prepared. The spectra were taken up with the pellets on a Perkin-Elmer 257 spectrophotometer. The characteristic bands of the infrared spectrum of N-methyl-N'{2-[(5-methylimidazol-4-yl)-methylthio]-ethyl}-N''-cyanoguanidine Z are as follows. A sharply outlined signal of medium intensity is found at 3300 cm$^{-1}$ followed by a slightly stronger band couple coalescing at 3210 and 3180 cm$^{-1}$, respectively. An undistinctive, little peak is observed at 3100 to 2800 cm$^{-1}$. The C=N signal appears at 2155 cm$^{-1}$. The characteristic feature of the new crystal modification is the band couple of high intensity at 1610 and 1585 cm$^{-1}$ that can be assigned to the C=N. bonds.

In the "finger-print" spectral range, the doublet band couple of medium intensity at 952 and 942 cm$^{-1}$ is unambiguously characteristic. This typical band does not occur at other modifications.

Additional characteristic bands are found at 1205, 1170, 1070, 1023, 890, 817 and 755 cm$^{-1}$. The spectrum is shown in FIG. 2 enclosed.

Powder diagram and mono-crystal X-ray diffraction studies were also performed with the new crystal modification. The powder diagrams were taken up on a Zeiss HZG 4/c instrument (Cu tube, 40kV, 20 mA, Ni filter, at a rate of 1°/min of the goniometer and at a rate of 1 cm/min of the paper). The values of distances of lattice planes and relative intensities as calculated from the X-ray diamgram (FIG. 1 enclosed) are given in the following Table.

| pm | $I/I_O$ % | pm | $I/I_O$ % | pm | $I/I_O$ % |
| --- | --- | --- | --- | --- | --- |
| 684 | 34 | 405 | 5 | 296.2 | 6 |
| 642 | 36 | 402 | 5 | 292.6 | 3 |
| 605 | 77 | 390 | 16 | 289.1 | 7 |
| 576 | 3 | 388 | 17 | 276.7 | 15 |
| 540 | 5 | 381 | 15 | 271.2 | 20 |
| 513 | 38 | 363 | 7 | 268.8 | 8 |
| 482 | 15 | 352 | 52 | 260.4 | 6 |
| 468 | 6 | 346 | 100 | 256.3 | 10 |
| 449 | 10 | 329 | 59 | 252.6 | 9 |
| 433 | 20 | 322 | 42 | 240.3 | 5 |
| 424 | 28 | 315 | 2 | 231.7 | 4 |
| 415 | 30 | 307 | 29 | 224.8 | 9 |

The monocrystal studies were carried out with an ENRAF NONIUS CAD-4 diffractometer.

Hädicke et al. [Chem. Ber. 111, 3222 (1978)] published their results of X-ray diffraction measurements on the crystal modification A of N-methyl-N'-{2-[(5-methylimidazol-4-yl)-methylthio]-N''-cyanoguanidine. The crystal structure declared by them is unambiguous: an intramolecular hydrogen bond exists between the atoms N2 and N4 of the molecule. Thus, the molecule of this crystal modification forms a cyclic structure extending to about a distance of 10 atoms. The gravimetric density as concluded from the cell volume amounts to 420 g/l.

The torsion angles (in degrees) calculated from the monocrystal X-ray diagram of N-methyl-N'-{2-[(5-methylimidazol-4-yl)-methylthio]-ethyl}-N''-cyanoguanidine Z are as follows.

[The numbering of the atoms is shown in Formula (I).]

| | |
| --- | --- |
| N2-C2-C5-S1 | −49.4 |

-continued

| | |
|---|---|
| C3-C2-C5-S1 | 129.8 |
| C2-C5-S1-C6 | −45.2 |
| C5-S1-C6-C7 | −69.8 |
| S1-C6-C7-N3 | −60.1 |
| C6-C7-N3-C8 | 110.1 |
| C7-N3-C8-N4 | 179.2 |
| C7-N3-C8-N5 | −0.1 |
| N3-C8-N4-C9 | −7.6 |
| N5-C8-N4-C9 | 171.7 |
| N3-C8-N5-C10 | 167.6 |
| N4-C8-N5-C10 | −11.7 |
| C8-N5-C10-N6 | −173.7 |

It arises from the torsion angles of the new modification that no hydrogen bond exists between either the N2 and N4 or other atoms of the molecule but the molecule forms a substantially linear structure leading to a smaller cell volume which in turn results in an increased gravimetric density of 680 g/l as weighed macroscopically. This is advantageous from a pharmaceutical point of view, too.

The new crystal modification discovered by us can be prepared in the practice from a solution containing water or water together with a water-miscible organic solvent, if the supersaturation needed to the crystal precipitation is accomplished at a temperature range between 20° and 40° C. When carrying out the crystallization above 40° C. or below 20° C., the contamination of the product with other crystal modifications has to be considered.

The supersaturation can be realized by portioning a hot solution of N-methyl-N'-{2-[(5-methylimidazol-4-yl)-methylthio]-ethyl}-N''-cyanoguanidine in a colder solution and by cooling or salting out a solution of N-methyl-N'-{2-[(5-methylimidazol-4-yl)-methylthio]-ethyl}-N''-cyanoguanidine. Moreover, the supersaturation can be reached in such a way that a well-soluble salt of N-methyl-N'-{2-[(5-methylimidazol-4-yl)-methylthio]-ethyl}-N''-cyanoguanidine base formed with a mineral or organic acid is reacted with alkali hydroxides or other basic materials. On salt formation, the pH is adjusted to a value not lower than 4, preferably above 5, in order to avoid any decomposition process. The base is portioned in such a way that the pH level is maintained at a value not higher than about 10, preferably at about 9.

For promoting the formation of crystal nuclei, the supersaturated solution may contain a water-miscible organic solvent, preferably in an amount of 0.1 to 5%.

The preparation of N-methyl-N'{2-[(5-methylimidazol-4-yl)-methylthio]-ethyl}-N''-cyanoguanidine Z is illustrated by the following non-limiting Examples.

EXAMPLE 1

200.0 g (0.696 mole) of N-cyano-N'-{2-[(5-methyl-4-imidazolyl)-methylthio]-ethyl}-S-methylisothiourea, 650.0 ml of distilled water and 220.0 g (3.244 moles) of 40% aqueous methylamine are weighed in a flask of 2 l volume. The reaction mixture is heated to 55° C. and stirred for one hour at this temperature. During this period methyl mercaptan leaves in an amount of about 55% of the theoretical quantity.

Then 210.0 ml of acetic acid are portionwise added to the reaction mixture while maintaining the temperature at 40° to 50° C. by cooling. A homogeneous solution is formed with a pH value of 5.8 to 6.3. A further amount of 44.5% of methyl mercaptan leaves during the addition of the acetic acid.

After dissolution of the base formed, the solution is clarified by 3.0 g of activated carbon, filtered, cooled to 25° C. and the pH value is adjusted to 9 by adding 130.0 ml of concentrated aqueous ammonium hydroxide solution. The precipitation of the new crystal modification of N-methyl-N'-{2-[(5-methylimidazol-4-yl)-methylthio]-ethyl}-N''-cyanoguanidine starts. After complete precipitation the mixture is cooled to 0° C., filtered and washed with water cooled to 0° C. The wet weight of the product is 175.35 g, the dry weight is 167.0 g (95.10%); m.p. 139° to 141° C.

EXAMPLE 2

The process described in Example 1 is followed, except that 50.0 ml of methanol are added after adding acetic acid and cooling the mixture to 35° C., and than the product is precipitated by concentrated aqueous ammonium hydroxide solution. After cooling to 0° C. the mixture is filtered and washed with cooled water. The wet weight of the product is 176.30 g, the dry weight is 165.76 g (94.4%); m.p. 139° to 141° C.

EXAMPLE 3

14.35 g (0.05 mole) of N-cyano-N'-{2-[(5-methyl-4-imidazolyl)-methylthio]-ethyl}-S-methylisothiourea, 50.0 ml of distilled water and 18.5 ml (0.21 mole) of aqueous methylamine solution (with a concentration of 11.5 moles/l) are placed in a round-bottom flask and the mixture is stirred at 50° to 55° C. for 2.5 hours and then at 80° to 85° C. for 30 minutes. The thus-obtained homogeneous solution is poured into 35.0 ml of water maintained at a temperature of 0° to 5° C. by using strong external cooling. The temperature increases to 30° C. as a maximum and a well-settling and well-filtrable product is precipitated. The suspension is cooled to 0° C. while stirring, filtered and washed with water cooled to 0° C. The wet weight of the product is 14.3 g, the dry weight is 11.51 g (90.5%); m.p. 139° to 141° C.

EXAMPLE 4

A solution containing 25. 24 g (0.100 mole) of N-methyl-N'-{2-[(5-methylimidazol-4-yl)-methylthio]-ethyl}-N'-cyanoguanidine is prepared with 200.0 ml of distilled water and the pH value of the solution is adjusted to 6 by acetic acid. Then 10.0 ml of acetone are added and the pH is adjusted to 10 by 10% sodium carbonate solution of 25° to 30° C. Crystals are precipitated which settle well and are easily filtered.

After cooling to 0° C., the precipitated product is filtered and washed with cooled water. The wet weight of the product is 26.00 g, the dry weight is 24.30 g (96.20%); m.p. 140° to 141° C.

EXAMPLE 5

A solution containing 25.24 g (0.100 mole) of N-methyl-N'-{2-[(5-methylimidazol-4-yl)-methylthio]-ethyl}-N''-cyanoguanidine is prepared with 200.0 ml of distilled water and the pH value of the solution is adjusted to 6 by concentrated formic acid.

5.0 ml of methanol are added and the pH is brought to 10 by concentrated ammonium hydroxide at 25° to 30° C. The crystalline precipitate settles rapidly and can easily be filtered. After cooling to 0° C. the crystals are collected by filtration and washed with cooled water. The wet weight of the product is 26.40 g, the dry weight is 24.23 g (95.7%); m.p. 140° to 141° C.

EXAMPLE 6

The pH value of a solution of 12.62 g (0.05 mole) of N-methyl-N'-{2-[(5-methylimidazol-4-yl)-methylthio]-ethyl}-N''-cyanoguanidine in 100.0 ml of distilled water is adjusted to pH 6 to 6.3 with a citric acid solution of 10% concentration and then worked up according to Example 5. The wet weight of the product is 13.1 g, the dry weight is 12.0 g (95.2%); m.p. 140° to 141° C.

EXAMPLE 7

The pH value of a solution of 25.24 g (0.100 mole) of N-methyl-N'-{2-[(5-methylimidazol-4-yl)-methylthio]-ethyl}-N''-cyanoguanidine in 200.0 ml of distilled water is adjusted to 5.8 to 6.0 by phosphoric acid of 85% and then worked up according to Example 5. The wet weight of the product is 25.50 g, the dry weight is 24.2 g (95.4%); m.p. 140° to 141° C.

EXAMPLE 8

The pH value of a solution of 25.24 g (0.100 mole) of N-methyl-N'-{2-[(5-methylimidazol-4-yl)-methylthio]-ethyl}-N''-cyanoguanidine in 200.0 ml of distilled water is adjusted to 6 by propionic acid and then worked up according to Example 5. The wet weight of the product is 26.05 g, the dry weight is 23.90 g (94.6%); m.p. 140° to 141° C.

EXAMPLE 9

The pH value of a suspension of 20.0 g (0.0696 mole) of N-methyl-N'-{2-[(5-methylimidazol-4-yl)-methylthio]-ethyl}-N''-cyanoguanidine in 60.0 ml of an 1:1 mixture of methanol with water is brought to 5.8 to 6.0 with concentrated acetic acid solution. The homogeneous solution thus obtained is cooled to 0° C., seeded with a crystal of N-methyl-N'-{2-[(5-methylimidazol-4-yl)-methylthio]-ethyl}-N''-cyanoguanidine Z and then the pH is adjusted to 9 to 10 at the same temperature with concentrated ammonium hydroxide solution. After cooling at 0° C. for one hour the precipitate is filtered and washed with water cooled to 0° C. The wet weight of the product is 20.80 g, the dry weight is 19.26 g (96.30%); m.p. 140° to 141° C.

EXAMPLE 10

A solution is prepared from 20.0 g (0.0696 mole) of N-methyl-N'-{2-[(5-methylimidazol-4-yl)-methylthio]-ethyl}-N''-cyanoguanidine in 120.0 ml of methanol at 38° C., seeded with a crystal of N-methyl-N'-{2-[(5-methylimidazol-4-yl)-methylthio]-ethyl}-N''-cyanoguanidine Z, cooled to 0° C. during 2 hours, stirred at the same temperature for one hour, filtered and washed with cooled methanol. The wet weight of the product is 19.78 g, the dry weight is 19.02 g (95.1%); m.p. 140.5° to 141° C.

What we claim is:

1. N-methyl-N'-{2-[(5-methylimidazol-4-yl)-methylthio]-ethyl}-N''-cyanoguanidine (modification Z).

2. Cimetidine Z, the IR-spectrum of which is characterized by the following absorption bands: 3208, 3186, 2153, 1612, 1587, 1449, 1377, 1347, 1170, 954, 943, 756, 660 and 625 cm$^{-1}$, and its powder radiogram by the common occurrence of reflections of significant intensity to be observed at the following layer distances provided in A: 6.82, 6.42, 6.00, 5.10, 4.82, 4.34, 4.23, 3.80, 3.51, 3.46, 3.30, 3.23 and 2.71.

3. A composition for producing the histamine H-2 receptor antagonist modification A which comprises an effective amount of the crystal modification Z of N-methyl-N'-2-[(5-methylimidazol-4-yl)-methylthio]-ethyl-N''-cyanoguanidine in association with a pharmaceutically acceptable carrier and/or excipient.

* * * * *